United States Patent
Song et al.

(10) Patent No.: US 9,251,611 B2
(45) Date of Patent: Feb. 2, 2016

(54) METHOD AND APPARATUS FOR MEDICAL IMAGE DISPLAY, AND USER INTERFACE SCREEN GENERATING METHOD

(71) Applicant: SAMSUNG MEDISON CO., LTD., Gangwon-do (KR)

(72) Inventors: Joo-hyun Song, Gangwon-do (KR); Jong-sik Kim, Gangwon-Do (KR); Jin-yong Lee, Gangwon-Do (KR); Jae-moon Jo, Gangwon-Do (KR)

(73) Assignee: Samsung Medison Co., Ltd., Gangwon-do (KR)

( * ) Notice: Subject to any disclaimer, the term of this patent is extended or adjusted under 35 U.S.C. 154(b) by 126 days.

(21) Appl. No.: 14/050,214

(22) Filed: Oct. 9, 2013

(65) Prior Publication Data
US 2014/0104281 A1   Apr. 17, 2014

(30) Foreign Application Priority Data

Oct. 11, 2012 (KR) .................. 10-2012-0113036

(51) Int. Cl.
*G06T 11/20* (2006.01)
*A61B 8/08* (2006.01)
*A61B 8/00* (2006.01)

(52) U.S. Cl.
CPC .............. *G06T 11/206* (2013.01); *A61B 8/0883* (2013.01); *A61B 8/463* (2013.01); *A61B 8/485* (2013.01); *A61B 8/5215* (2013.01); *G06T 11/20* (2013.01); *A61B 2576/023* (2013.01)

(58) Field of Classification Search
CPC .. G01S 15/8993; A61B 5/055; A61B 8/0883; A61B 5/06; G06T 7/0012; G06T 11/001; G06T 2201/0051; G06T 2207/10016; G06T 11/206; G06T 15/005; G06T 11/40; G06T 11/203; G06K 9/00127; G09G 3/3688

USPC ......... 345/156, 204, 208, 418, 419, 420, 424, 345/440, 441, 442, 501, 581; 382/100, 103, 382/108, 128, 131, 132, 133, 134, 154, 162, 382/168, 171, 173; 600/109, 111, 410, 421, 600/424, 425, 426, 443, 450
See application file for complete search history.

(56) References Cited

U.S. PATENT DOCUMENTS

| 5,820,561 A | 10/1998 | Olstad et al. |
| 6,053,869 A | 4/2000 | Kawagishi et al. |

(Continued)

FOREIGN PATENT DOCUMENTS

| JP | 11-125549 A | 5/1999 |
| JP | 11-155862 A | 6/1999 |

(Continued)

OTHER PUBLICATIONS

Dandel, Michael, et al. "Strain and Strain Rate Imaging by Echocardiography—Basic Concepts and Clinical Applicability." Current Cardiology Reviews 5.2 , Bentham Science Publishers Ltd., (2009): pp. 133-148.*

(Continued)

*Primary Examiner* — Xiao Wu
*Assistant Examiner* — Sarah Lhymn
(74) *Attorney, Agent, or Firm* — McDermott Will & Emery LLP (57) ABSTRACT

A cardiac ultrasound image display to analyze a heart wall motion, and a method and apparatus for displaying a cardiac ultrasound image. A method of displaying a medical image includes obtaining a characteristic value for each of one or more segments included in an object, generating an image of the object indicating the segment of which the characteristic value is a predetermined value, and displaying the image.

18 Claims, 5 Drawing Sheets

(56) References Cited

U.S. PATENT DOCUMENTS

| | | | |
|---|---|---|---|
| 7,245,746 | B2 | 7/2007 | Bjaerum et al. |
| 2002/0186868 | A1* | 12/2002 | Bjaerum et al. ............... 382/128 |
| 2007/0258631 | A1* | 11/2007 | Friedman et al. ............. 382/128 |
| 2007/0258632 | A1 | 11/2007 | Friedman et al. |
| 2008/0021318 | A1* | 1/2008 | Kato .................. A61B 5/02007 600/437 |
| 2008/0081997 | A1 | 4/2008 | Kakihara |
| 2009/0069680 | A1 | 3/2009 | Abe |
| 2009/0281424 | A1* | 11/2009 | Friedman et al. ............. 600/438 |
| 2009/0318803 | A1* | 12/2009 | Abe .................... A61B 8/0883 600/438 |
| 2010/0041992 | A1 | 2/2010 | Ohuchi et al. |
| 2011/0098562 | A1 | 4/2011 | Salgo et al. |
| 2011/0098563 | A1* | 4/2011 | Osaka ........................... 600/438 |

FOREIGN PATENT DOCUMENTS

| | | |
|---|---|---|
| JP | 2006-026079 A | 2/2006 |
| JP | 2010-042151 A | 2/2010 |
| JP | 2011-527586 A | 11/2011 |
| JP | 2012-187383 A | 10/2012 |

OTHER PUBLICATIONS

Korean Office Action issued in Korean Applictation No. KR10-2012-0113036 dated Jul. 1, 2014, with English translation.

Extended European Search Report issued in European Application No. 13181523.5 dated Jan. 23, 2014.

Notice of Allowance issued in Korean Application No. 10-2012-0113036 dated Jan. 5, 2015, with English translation.

* cited by examiner

METHOD AND APPARATUS FOR MEDICAL IMAGE DISPLAY, AND USER INTERFACE SCREEN GENERATING METHOD

CROSS-REFERENCE TO RELATED PATENT APPLICATION

This application claims the benefit of Korean Patent Application No. 10-2012-0113036, filed on Oct. 11, 2012, in the Korean Intellectual Property Office, the disclosure of which is incorporated herein in its entirety by reference.

BACKGROUND OF THE DISCLOSURE

1. Field of the Disclosure

The present disclosure relates to a method and apparatus for a medical image display, and more particularly, to a cardiac ultrasound image display to analyze a heart wall motion, and a method and apparatus for displaying a cardiac ultrasound image.

2. Description of the Related Art

In the ultrasound image display field, displaying a tissue deformation characteristic such as strain and a strain rate of a local portion of a target object provides a direct and quantitative measurement standard about the ability of a muscle that strains and relaxes.

In particular, displaying a real-time strain rate of a muscle as an image may be applied in cardiology. Analyzing a tissue deformation characteristic such as strain and a strain rate of a heart muscle is referred to as a strain and strain rate analysis. Although a healthy heart does not have a movement disorder at a local portion, that is, a segment, a heart suffering from a heart disease shows a difference in a strain movement between segments of a heart wall, particularly a difference in strain timing. Thus, whether the segments of a heart wall move simultaneously is one of the important factors to diagnose a cardiac disease.

According to a conventional technology, a degree of strain of a segment is indicated by colors on a 2D mode image of a heart to analyze a heart wall motion. However, when the degree of strain of each segment of a heart wall is indicated by colors on a 2D image as in the conventional technology, strain timing between segments of a heart wall may not be accurately identified. Accordingly, in addition to the 2D image corresponding to a heart, separate medical examination material needs to also be checked, which is inconvenient. For example, a time-strain graph needs to be inconveniently obtained and referred to, aside from the 2D image, to check a peak time point of each segment, i.e., an accurate time point when a segment strains most and a temporal difference in peak time points between the segments. These are important determination standards for a heart wall motion analysis.

SUMMARY OF THE DISCLOSURE

The present disclosure provides a method and apparatus for displaying a medical image which enables a fast and accurate check-up of whether segments of a heart wall move simultaneously in a heart wall motion analysis for a doctor to diagnose a heart disease.

The present disclosure provides a method and apparatus for displaying a medical image which enables a fast and accurate diagnosis on a heart wall motion through a cardiac ultrasound image, and a method of generating a user interface screen.

Particularly, the present disclosure provides a method and apparatus for displaying a medical image which enables a fast and accurate check-up of whether segments of a heart wall move simultaneously in a heart wall motion analysis, and a method of generating a user interface screen.

According to an aspect of the present disclosure, a method of displaying a medical image includes obtaining a characteristic value for each of one or more segments included in an object, generating an image of the object indicating the segment of which the characteristic value is a predetermined value, and displaying the image.

The step of generating an image may include generating the image distinguishably indicating a segment of which the characteristic value is the predetermined value and a segment of which the characteristic value is not the predetermined value.

The step of generating an image may include generating the image distinguishably indicating a segment before the characteristic value reaches the predetermined value, a segment of which the characteristic value is the predetermined value, and a segment after the characteristic value reaches the predetermined value.

The step of generating an image may include generating the image including information that indicates a time when the characteristic value reaches the predetermined value.

The information indicating the time may include a difference between a reference time and an actual time when the characteristic value reaches the predetermined value.

When two or more segments exist in the step of obtaining a characteristic value, the reference time may be a time when an average of the characteristic values of the segments reaches the predetermined value.

The object may include a heart, the one or more segments may include a predetermined area of a heart wall of the heart, and the characteristic value may include a myocardial strain rate.

The predetermined value may be a peak value of the characteristic value.

According to another aspect of the present disclosure, an apparatus for displaying a medical image includes a characteristic value obtaining unit for obtaining, using a processor, a characteristic value for each of one or more segments included in an object, an image generating unit generating an image of the object indicating the segment of which the characteristic value is a predetermined value, and a display unit displaying the image.

According to another aspect of the present disclosure, a method of generating a user interface screen includes generating a user interface screen including an image of an object indicating at least one segment of which a characteristic value is a predetermined value, wherein the at least one segment is included in the object, and displaying the user interface screen.

BRIEF DESCRIPTION OF THE DRAWINGS

The above and other features and advantages of the present disclosure will become more apparent by describing in detail exemplary embodiments thereof with reference to the attached drawings in which.

DETAILED DESCRIPTION OF THE DISCLOSURE

The terms used in the present specification are for explaining a specific exemplary embodiment of the disclosure, and are not limiting of the present inventive concepts. Thus, the expression of singularity in the present specification includes the expression of plurality unless clearly specified otherwise in context. Unless defined otherwise, all terms used herein including technical or scientific terms have the same meanings as those generally understood by those having ordinary skill in the art to which the present inventive concepts may pertain. Terms defined in generally used dictionaries are construed to have meanings matching that in the context of related technology and, unless clearly defined otherwise, are not construed to be ideally or excessively formal.

When a part may "include" a certain constituent element, unless specified otherwise, it may not be construed to exclude other constituent elements but may be construed to further include other constituent elements. Terms such as "~portion", "~unit", "~module", and "~block" stated in the specification may signify a structure to process at least one function or operation and the structure may be embodied by hardware (e.g., a processor), software, or a combination of hardware and software.

The attached drawings for illustrating exemplary embodiments of the present disclosure are referred to in order to gain a sufficient understanding of the present disclosure, the merits thereof, and the objectives which can be accomplished by the implementation of the present disclosure. Hereinafter, the present disclosure will be described in detail by explaining exemplary, non-limiting embodiments of the disclosure with reference to the attached drawings. To clearly describe the present disclosure, portions that are not related to the description of the present disclosure may be omitted herein. Throughout the specification, like reference numerals in the drawings denote like elements.

Expressions such as "at least one of" or "at least part of," when preceding a list of elements, modifies the entire list of elements and does not modify the individual elements of the list.

As one of the exemplary methods for diagnosing a heart disease, an ultrasound signal is transmitted toward a heart by using an ultrasound system, and then an image of a heart section is obtained from information derived from the ultrasound signal reflected by tissues in a body. The analysis of an ultrasound image obtained by the ultrasound system and the displaying of a tissue deformation characteristic, such as strain and a strain rate of each segment of a heart wall, provide a direct and quantitative measurement standard about the ability of a muscle that strains and relaxes.

With reference to the accompanying drawings, methods and apparatuses for displaying a medical image according to a variety of exemplary embodiments of the present disclosure, which enable a fast and accurate heart wall motion analysis for a doctor to diagnose a heart disease, and a method of generating a user interface screen, are described in detail.

Figure 1:
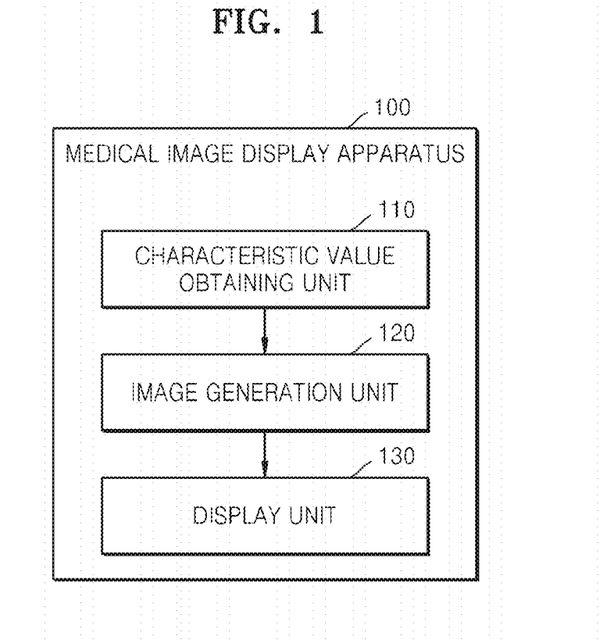
FIG. 1 is a block diagram illustrating a medical image display apparatus according to an exemplary embodiment of the present disclosure.

FIG. 1 is a block diagram illustrating a medical image display apparatus 100 according to an exemplary embodiment of the present disclosure. Referring to FIG. 1, the medical image display apparatus 100 includes a characteristic value obtaining unit 110, an image generation unit 120, and a display unit 130. The medical image display apparatus 100 may further include other elements such as an ultrasound signal generation and receiving unit (not shown) and a probe (not shown).

The characteristic value obtaining unit 110 obtains a characteristic value(s) for a segment included in an object. For example, the characteristic value obtaining unit 110 may generate an image about a section of soft tissue or a bloodstream of soft tissue and obtain a characteristic value such as a strain rate of muscle, by using the information of an ultrasound signal transmitted toward an object and reflected from tissues in the object.

In detail, when the medical image display apparatus 100 further includes an ultrasound signal generation and receiving unit (not shown), the ultrasound signal generation and receiving unit generates an ultrasound signal and outputs the generated ultrasound signal through a probe (not shown). The ultrasound signal generation and receiving unit then receives a reflected ultrasound signal through the probe. For example, the probe transmits the ultrasound signal generated by the ultrasound signal generation and receiving unit to an object that is a target internal organ, and receives the reflected ultrasound signal corresponding to a transferred ultrasound signal and transfers the signal to the ultrasound signal generation and receiving unit.

Then, the characteristic value obtaining unit 110 may obtain a predetermined characteristic value for each segment by using the reflected ultrasound signal received through the probe. Also, the characteristic value obtaining unit 110 may generate an ultrasound image corresponding to the object.

The segment may refer to a local portion of the object and may be uniformly designated by the medical image display apparatus 100 or individually designated by a user. For example, for a heart wall, six (6) portions that are uniformly divided around an apex of the heart wall may be designated as segments.

The image generation unit 120 generates an image of the object indicating the segment of which the characteristic value obtained by the characteristic value obtaining unit 110 is a predetermined value. The display unit 130 displays the image generated by the image generation unit 120.

The segment of which a characteristic value is a predetermined value may be a segment whose characteristic value is determined to be a maximum value, a minimum value, or a middle value within a predetermined time, for example, a cardiac cycle. Also, the segment of which a characteristic value is a predetermined value may signify a segment in which, when the characteristic value is in a range of a certain parameter, for example, when the characteristic value is a myocardial strain, the myocardial strain is within a predetermined percentage range. The predetermined value may be a peak value of the characteristic values, that is, the maximum value within a predetermined time.

Also, the image generated by the image generation unit 120 may be an image of the object in which a segment is marked by any one of a predetermined color, shape, and sign, or is presented to blink, which will be described below with reference to FIGS. 4A through 6.

Also, the image generation unit 120 may generate an image that further indicates a segment of which a characteristic value obtained from the characteristic value obtaining unit 110 is not a predetermined value, in addition to the segment of which the characteristic value is a predetermined value. The segment having the characteristic value that is a predetermined value and the segment having the characteristic value that is not a predetermined value may be distinguishably indicated, which will be described below with reference to FIGS. 4A to 4C.

Also, the image generation unit 120 may generate an image that further indicates a segment whose characteristic value obtained from the characteristic value obtaining unit 110 does not reach a predetermined value and a segment whose characteristic value has reached the predetermined value, in addition to the segment in which the characteristic value is the predetermined value. The segment whose characteristic value has not yet reached a predetermined value and the segment whose characteristic value has already reached the predetermined value may be distinguishably indicated, which will be described below with reference to FIG. 5.

For example, to distinguishably indicate segments in an image generated by the image generation unit 120, each segment may be indicated by a different color, shape, or sign.

The image generation unit 120 may include information indicating a time at which a characteristic value reaches a predetermined value. The information indicating the time may include a difference between a reference time and an actual time when the characteristic value reaches the predetermined value. When there are two or more segments of which characteristic values are obtained by the characteristic value obtaining unit 110, the reference time may be a time when an average of the characteristic values of the segments reaches the predetermined value, which will be described below with reference to FIG. 6.

The object of which a characteristic value is obtained by the characteristic value obtaining unit 110 may be a heart. A myocardial strain with respect to at least one segment of a heart wall of a heart may be obtained as a characteristic value.

Figure 2:
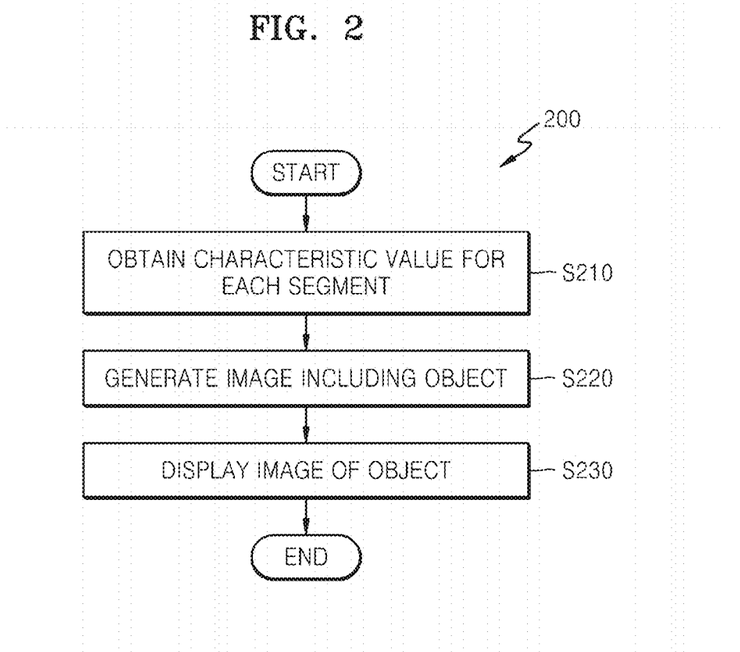
FIG. 2 is a flowchart explaining a medical image display method according to an exemplary embodiment of the present disclosure.

FIG. 2 is a flowchart for explaining a medical image display method 200 according to an exemplary embodiment of the present disclosure. The medical image display method 200 of FIG. 2 may be performed using the medical image display apparatus 100 of FIG. 1. Each step of the medical image display method 200 may have the same technical concept as that of each constituent operation performed by the structural elements of the medical image display apparatus 100. Thus, a description that is the same as the description for FIG. 1 is omitted. In the following description, the medical image display method 200 is described referring to the medical image display apparatus 100 of FIG. 1.

Referring to FIG. 2, the medical image display apparatus 100 obtains a characteristic value for each of at least one segment included in an object at S210. The step S210 may be performed by the characteristic value obtaining unit 110. The medical image display apparatus 100 generates an image of the object indicating a segment in which the characteristic value is a predetermined value at S220. The step S220 may be performed by the image generation unit 120. Also, the medical image display apparatus 100 displays a generated image at S230. The step S230 may be performed by the display unit 130.

Figure 3:
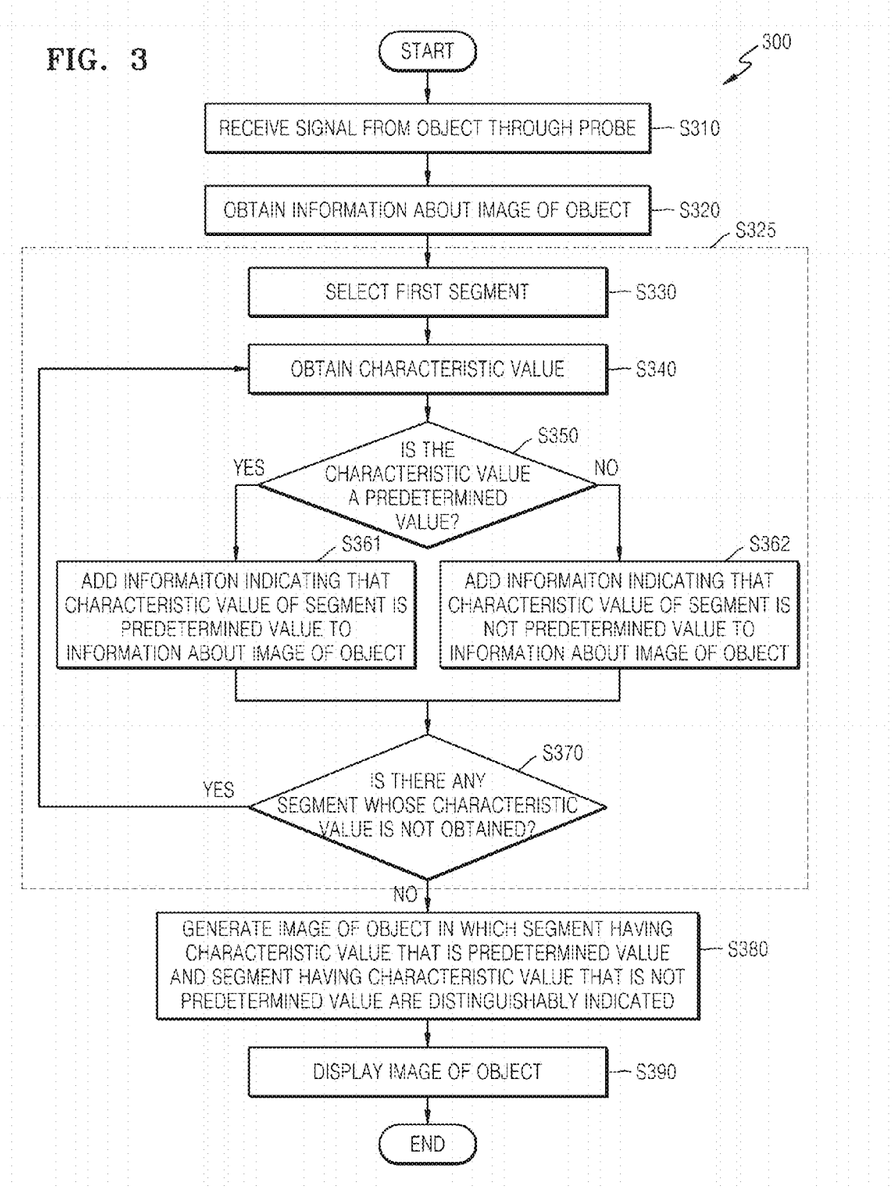
FIG. 3 is a flowchart explaining a medical image display method according to another exemplary embodiment of the present disclosure.

FIG. 3 is a flowchart for explaining a medical image display method 300 according to another exemplary embodiment of the present disclosure. Referring to FIG. 3, the medical image display method 300 includes steps that are processed by the characteristic value obtaining unit 110, the image generation unit 120, and the display unit 130 of the medical image display apparatus 100 of FIG. 1. Also, the step S325 of FIG. 3 corresponds to the step S210 of FIG. 2, the step S380 of FIG. 3 corresponds to the step S220 of FIG. 2, and the step S390 of FIG. 3 corresponds to the step S230 of FIG. 2. Thus, although omitted herein, it may be seen that the above descriptions about the constituent elements shown in FIGS. 1 and 2 can also be applied to the flowchart of FIG. 3.

Referring to FIG. 3, the medical image display apparatus 100 may receive a signal from the object through the probe at S310. For example, the medical image display apparatus 100 may generate an ultrasound signal, which for example is generally 20 kHz or higher, and may receive information of a reflected echo signal by using the probe.

The medical image display apparatus 100 may obtain information about the image of the object at S320, select a first segment among the at least one segment included in the object at S330, obtain a characteristic value of a selected segment at S340 from the signal received in the step S310, and determine whether the characteristic value is a predetermined value at S350.

In the step S350, if the characteristic value of a segment is determined to be the predetermined value, information indicating that the characteristic value of the segment is the predetermined value may be added to the information about the image of the object at S361. If the characteristic value of a segment is not determined to be the predetermined value, information indicating that the characteristic value of the segment is not the predetermined value may be added to the information about the image of the object at S362.

Next, the medical image display apparatus 100 may determine whether there is any remaining segment whose characteristic value is not obtained at S370. If it is determined that a remaining segment(s) whose characteristic value is not obtained exists, the medical image display apparatus 100 goes back to the step S340 of obtaining the characteristic value of a segment. If it is determined that there are no longer any segments whose characteristic value has not been obtained, the medical image display apparatus 100 proceeds to a step S380. In the step S380, an image is generated which distinguishably indicates the segment having the characteristic value that is the predetermined value and the segment having the characteristic value that is not the predetermined value. The generated object image is displayed at S390.

Figure 4A:
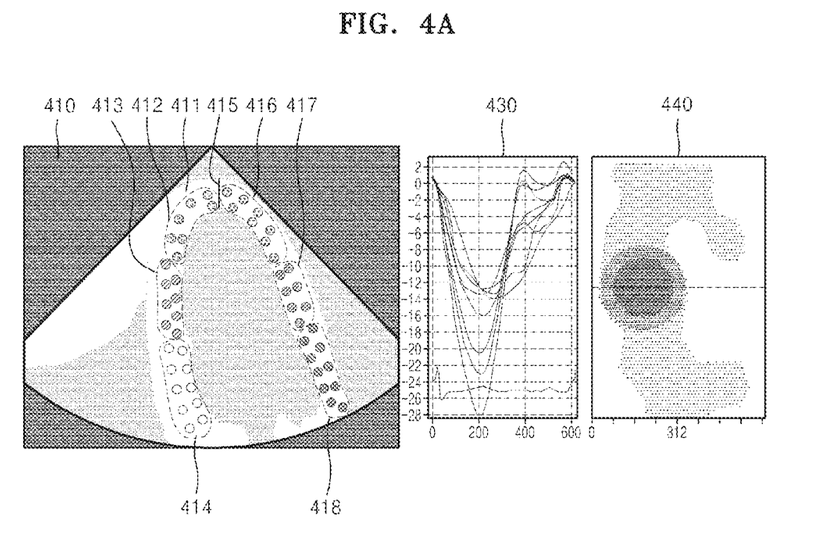
FIGS. 4A, 4B, and 4C are medical image displays according to an exemplary embodiment of the present disclosure.
Figure 4B:
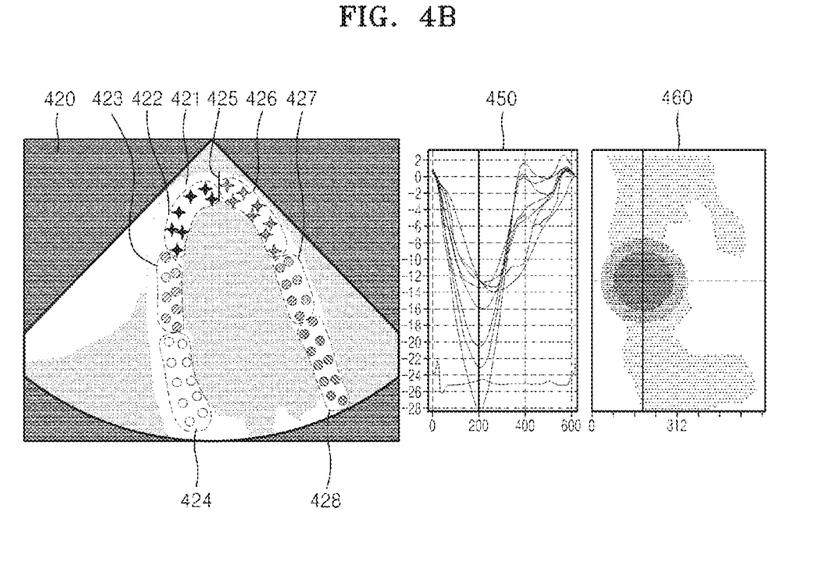
Figure 4C:
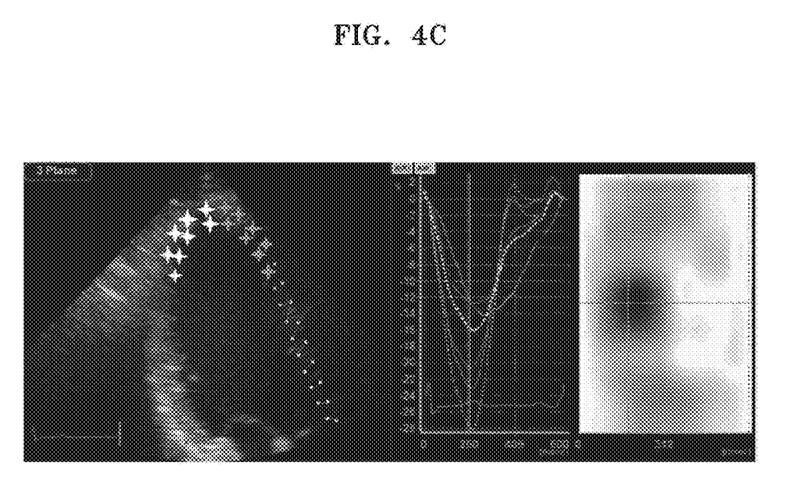

FIGS. 4A, 4B, and 4C show medical image displays according to an exemplary embodiment of the present disclosure. FIGS. 4A, 4B, and 4C illustrate ultrasound images of a heart wall which is divided into six (6) segments. In FIGS. 4A, 4B, and 4C, a segment of which the myocardial strain is a peak value and a segment of which the myocardial strain is not a peak value are distinguishably indicated, by obtaining a myocardial strain for each segment. FIG. 4A shows a medical image display before a heart wall strains. FIG. 4B shows a medical image display when a heart wall strains. FIG. 4C shows an actual image of FIG. 4B. The myocardial strain may be measured based on a difference between a reference length and the length of the measured muscle.

Referring to FIG. 4A, an ultrasound image 410 includes a heart wall 411. In FIG. 4A, the heart wall 411 is indicated by, for example, a plurality of dots. In detail, the left three (3) segments 412, 413, and 414 and the right three (3) segments 416, 417, and 418 with respect to an apex 415 are distinguishably indicated by different colored dots.

In the ultrasonic image 410 of FIG. 4A, a heart wall before getting strained is indicated by a plurality of circular points. The ultrasonic image 410 of FIG. 4A and the ultrasonic image 420 of FIG. 4B are referred to as a first image 410 and a second image 420, respectively.

Referring to FIG. 4B, in the second image 420, the myocardial strains of the segments 422 and 426 around the apex 425 reach a peak value sooner than the myocardial strains of other segments 423, 424, 427, and 428. In detail, when a myocardial strain reaches the peak value, the points in the segments 422 and 426 are changed from a circular shape to a star shape. Thus, the segments 422 and 426 of which the myocardial strains are the peak value and the segments 423, 424, 427, and 428 of which myocardial strains are not the peak value are distinguishably indicated by the different shape of the points.

The points indicating segments of a heart wall may return back to circular points as in the first image 410, when the segments have passed the peak, and completed a cardiac strain cycle and return to a basic state, for example, the starting point of the cardiac strain cycle. According to the present exemplary embodiment, as illustrated in FIGS. 4A, 4B, and 4C, the ultrasound images 410 and 420 of a heart wall may be displayed with relevant non-image graphs 430, 440, 450, and 460. The first non-image graphs 430 and 450 show the myocardial strains of segments, in which the x-axis and y-axis denote time and a myocardial strain, respectively. The second non-image graphs 440 and 460 signify an M mode image in an ultrasound diagnosis apparatus.

In the first non-image graphs 430 and 450 of FIGS. 4A and 4B, a global strain rate that is an average of the myocardial strains of the six segments of a heart wall, is calculated and displayed on the graphs with the myocardial strain of each segment.

Figure 5:
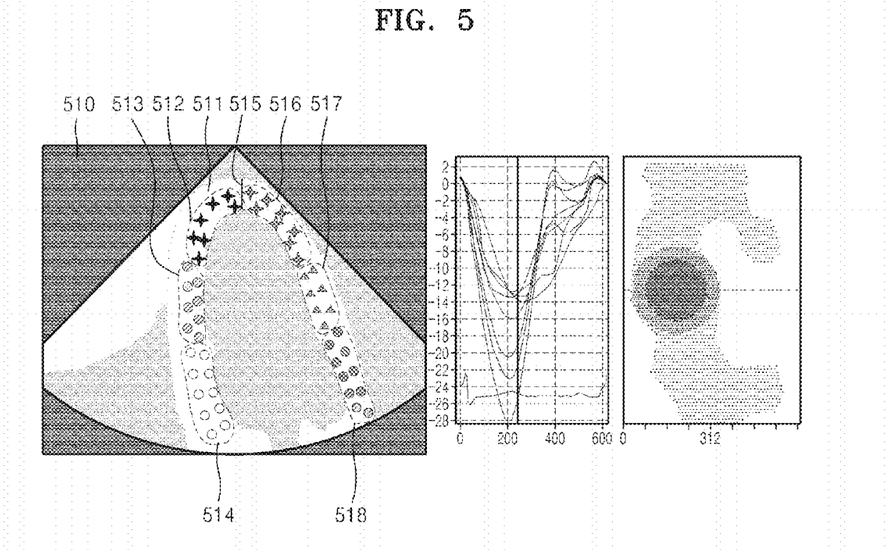
FIG. 5 is a medical image display according to another exemplary embodiment of the present disclosure.

FIG. 5 is a medical image display according to another exemplary embodiment of the present disclosure. FIG. 5 is an ultrasound image of a heart wall distinguishably displaying, by obtaining a myocardial strain for each of the six segments of a heart wall, a segment of which the myocardial strain has not yet reached the peak value, a segment of which the myocardial strain is the peak value, and a segment of which the myocardial strain has reached the peak value.

In the heart wall ultrasound image 510 of FIG. 5, segments 513, 514, and 518 of which the myocardial strains have not yet reached the peak values may be indicated by a plurality of circular points, segments 512 and 516 of which the myocardial strains are the peak value may be indicated by a plurality of star points, and a segment 517 of which the myocardial strain has reached the peak value may be indicated by a plurality of triangular points.

Figure 6:
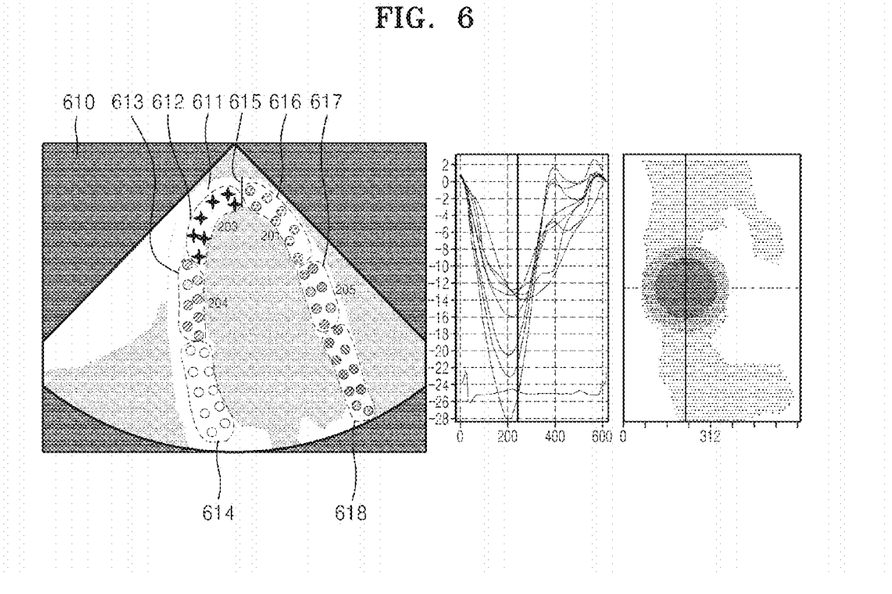
FIG. 6 is a medical image display according to another exemplary embodiment of the present disclosure.

FIG. 6 is a medical image display according to another exemplary embodiment of the present disclosure. As illustrated in FIG. 6, an ultrasound image display of a heart wall may selectively include information indicating a time when a myocardial strain of each segment reaches a peak value.

FIG. 6 is an ultrasound image 610 when a segment 612 is at a peak value. The ultrasound image 610 may further include information indicating a time when a myocardial strain of each segment reaches the peak value with respect to segments 612, 613, 616, and 617 selected by a user. Referring to FIG. 6, assuming that the starting point of a cardiac strain cycle is 0 ms, the strain rates of the segments 612, 613, 616, and 617 reach the peak value at 203 ms, 204 ms, 201 ms, and 205 ms, respectively.

According to another exemplary embodiment of the present disclosure, the information indicating the time when a myocardial strain of each segment reaches the peak value may be a time difference indicating how sooner (−time) or later (+time) the myocardial strain of each segment reaches the peak with respect to the peak time of the global strain rate.

The disclosure can also be embodied as computer readable codes on a computer readable recording medium. The computer readable recording medium is any data storage device that can store data which can be read by a computer system. Examples of a computer readable recording medium include read-only memory (ROM), random-access memory (RAM), CD-ROMs, magnetic tapes, floppy disks, optical data storage devices, etc. The computer readable recording medium can also be distributed over network coupled computer systems so that the computer readable code can be stored and executed in a distributed fashion. Also, functional programs, codes, and code segments for accomplishing the novel operations of the present disclosure can be construed by programmers having ordinary skill in the art to which the present disclosure pertains.

As described above, according to the present disclosure, since a characteristic value can be obtained from at least one segment included in an object and an image of the object indicating a segment where the characteristic value is a predetermined value can be generated and displayed, the order in which a characteristic value of each segment reaches the predetermined value may be identified faster and more accurately. As a result, whether the respective segments move with simultaneity may be intuitively identified.

While this disclosure has been particularly shown and described with reference to exemplary embodiments thereof, it will be understood by those having ordinary skill in the art that various changes in form and details may be made therein without departing from the spirit and scope of the disclosure as defined by the appended claims.

What is claimed is:

1. A method of displaying a medical image, the method comprising:
   obtaining a characteristic value for each of one or more segments included in an object;
   generating an image of the object indicating the segment of which the characteristic value is a predetermined value and including information that indicates a time when the characteristic value reaches the predetermined value; and
   displaying the image,
   wherein the segment and the time are displayed together on the image,
   wherein the information indicating the time includes a difference between a reference time and an actual time when the characteristic value reaches the predetermined value,
   wherein, when two or more segments exist in the step of obtaining a characteristic value, the reference time is a time when an average of the characteristic values of the segments reaches the predetermined value, and
   wherein the information indicating the time includes a time difference indicating how sooner or later the characteristic value reaches the predetermined value with respect to the reference time.

2. The method of claim 1, wherein the step of generating an image comprises generating the image distinguishably indicating a segment of which the characteristic value is the predetermined value and a segment of which the characteristic value is not the predetermined value.

3. The method of claim 1, wherein the step of generating an image comprises generating the image distinguishably indicating a segment before the characteristic value reaches the predetermined value, a segment of which the characteristic value is the predetermined value, and a segment after the characteristic value reaches the predetermined value.

4. The method of claim 1, wherein the object comprises a heart, the one or more segments comprises a predetermined area of a heart wall of the heart, and the characteristic value comprises a myocardial strain.

5. The method of claim 1, wherein the step of generating an image comprises generating the image in which the segment having the characteristic value that is the predetermined value is indicated by any one of a predetermined color, shape, and sign.

6. The method of claim 1, wherein the step of generating an image comprises generating the image in which the segment of which the characteristic value is the predetermined value is presented to blink.

7. The method of claim 1, wherein the predetermined value is a peak value of the characteristic value.

8. An apparatus for displaying a medical image, the apparatus comprising:
   a characteristic value obtaining unit for obtaining, using a processor, a characteristic value for each of one or more segments included in an object;
   an image generating unit for generating, using the processor, an image of the object indicating the segment of which the characteristic value is a predetermined value and including information that indicates a time when the characteristic value reaches the predetermined value; and
   a display unit displaying the image,
   wherein the segment and the time are displayed together on the image,
   wherein the information indicating the time includes a difference between a reference time and an actual time when the characteristic value reaches the predetermined value,
   wherein, when two or more segments exist, the reference time is a time when an average of the characteristic values of the segments reaches the predetermined value, and
   wherein the information indicating the time includes a time difference indicating how sooner or later the characteristic value reaches the predetermined value with respect to the reference time.

9. The apparatus of claim 8, wherein the image generating unit generates the image distinguishably indicating a segment of which the characteristic value is the predetermined value and a segment of which the characteristic value is not the predetermined value.

10. The apparatus of claim 8, wherein the image generating unit generates the image distinguishably indicating a segment before the characteristic value reaches the predetermined value, a segment of which the characteristic value is the predetermined value, and a segment after the characteristic value reaches the predetermined value.

11. The apparatus of claim 8, wherein the object comprises a heart, the one or more segments comprises a predetermined area of a heart wall of the heart, and the characteristic value comprises a myocardial rate.

12. The apparatus of claim 8, wherein the image generating unit generates the image in which the segment having the characteristic value that is the predetermined value is indicated by any one of a predetermined color, shape, and sign.

13. The apparatus of claim 8, wherein the image generating unit generates the image in which the segment of which the characteristic value is the predetermined value is presented to blink.

14. The apparatus of claim 8, wherein the predetermined value is a peak value of the characteristic value.

15. A method of generating a user interface screen, the method comprising:
   generating a user interface screen including an image of an object indicating at least one segment of which a characteristic value is a predetermined value and including information that indicates a time when the characteristic value reaches the predetermined value, wherein the at least one segment is included in the object; and
   displaying the user interface screen,
   wherein the segment and the time are displayed together on the image,
   wherein the information indicating the time includes a difference between a reference time and an actual time when the characteristic value reaches the predetermined value,
   wherein, when two or more segments exist, the reference time is a time when an average of the characteristic values of the segments reaches the predetermined value, and
   wherein the information indicating the time includes a time difference indicating how sooner or later the characteristic value reaches the predetermined value with respect to the reference time.

16. The method of claim 15, wherein the step of generating a user interface screen comprises generating the image distinguishably indicating a segment of which the characteristic value is the predetermined value and a segment of which the characteristic value is not the predetermined value, by any one of a predetermined color, shape, and sign.

17. The method of claim 15, wherein the predetermined value is a peak value of the characteristic value.

18. A non-transitory computer readable recording medium having recorded thereon a computer program for implementing the method of claim 1 or 15.

* * * * *